United States Patent [19]

Tanner et al.

[11] Patent Number: 5,125,923
[45] Date of Patent: Jun. 30, 1992

[54] LASER SURGICAL INSTRUMENT

[75] Inventors: Howard Tanner; James L. Sorenson, both of Salt Lake City, Utah

[73] Assignee: Sorenson Laboratories, Inc., Salt Lake City, Utah

[21] Appl. No.: 707,710

[22] Filed: May 30, 1991

[51] Int. Cl.⁵ .............................................. A61B 17/36
[52] U.S. Cl. ........................................ 606/10; 606/12; 128/397
[58] Field of Search ................ 128/6, 7, 395-398; 606/10-17

[56] References Cited

U.S. PATENT DOCUMENTS

| | | | |
|---|---|---|---|
| 3,195,536 | 7/1965 | Hovnanian et al. | 128/398 X |
| 4,316,467 | 2/1982 | Muckerheide | 606/16 X |
| 4,491,131 | 1/1985 | Vassiliadis | 606/10 |
| 4,492,230 | 1/1985 | Sunago et al. | 606/13 |
| 4,622,967 | 11/1986 | Schachar | 606/14 |
| 4,669,465 | 6/1987 | Moore et al. | 606/10 X |
| 4,712,537 | 12/1987 | Pender | 606/14 X |
| 4,715,372 | 12/1987 | Philippbar et al. | 606/10 X |
| 4,826,431 | 5/1989 | Fujimura et al. | 606/14 X |
| 4,920,961 | 5/1990 | Grossi et al. | 606/14 |
| 5,016,614 | 5/1991 | MacAllister | 128/6 X |

Primary Examiner—Peter A. Aschenbrenner
Attorney, Agent, or Firm—Trask, Britt & Rossa

[57] ABSTRACT

A laser surgical instrument is embodied as a handpiece supportable on the wrist and forearm of a surgeon. The handpiece is connected by an umbilical cord to a remote console. An internal shutter mechanism is actuated by steady finger pressure applied by the surgeon at a fixture grasped by the hand during use. An annular aiming beam is projected through an aperture in a physical distance gauge to focus concentric with the surgical laser beam.

28 Claims, 3 Drawing Sheets

LASER SURGICAL INSTRUMENT

BACKGROUND OF THE INVENTION

1. Field

This invention relates to laser surgery. It is particularly directed to a laser surgical instrument, and provides such an instrument which is supported in use by the hand and upper arm of a surgeon.

2. State of the Art

Laser surgery, as it is presently practiced in the fields of dermatology and podiatry, involves the use of hand-held instruments which attenuate a laser beam and direct the attenuated beam to an operative site. A typical such operative site comprises a tissue surface, such as the epidermis of a patient. These instruments are ordinarily powered from remote locations, and the requisite controls and monitoring devices are thus generally located remote from the surgeon. The hand-held instruments themselves are somewhat awkward to manipulate so that their use is characteristically accompanied by fatigue. Both the time period during which a surgical procedure must proceed and the efficiency of the procedure are limited because of this awkwardness.

Government regulations require the provision of two stage safety mechanisms in laser instruments. Conventionally, at least one of these stages has been provided as a foot switch, requiring a cord connection to the instrument and/or remote power supply.

There remains a need for improved hand-held instruments for the practice of laser surgical procedures.

SUMMARY OF THE INVENTION

According to this invention, a surgical laser instrument is configured and arranged to be supported by the surgeon atop his wrist and forearm As so arranged, the instrument is compact and convenient to transport from location to location. Moreover, the weight of the instrument is well supported and distributed with respect to the arm and wrist of a surgeon during use. Accordingly, the likelihood that a surgeon will experience fatigue during a surgical procedure is significantly reduced. The compact arrangement offered by the present invention is thus desirable from an ergomechanical standpoint.

In addition to its compact arrangement, certain embodiments of the present invention offer specific advantages over instruments heretofore available. Among these advantages are the provision of a mechanical distance gauge through which the surgical laser beam is projected. This gauge functions as a positive safety device to preserve a pre-established distance between the laser beam-emitting tip of the instrument and the operative site. Another feature provided by certain embodiments is a high intensity aiming beam transmitted coaxially with the laser beam. This light displays as an annular ring which defines the target area into which the focused laser beam is projected. The surgeon thus is always conscious of the specific region of a patient's tissue which is exposed to laser energy.

The device may be structured to display power readings directly at the handpiece rather than solely at a remote power supply. An output register device may be positioned so that it is readily visible to the surgeon during the course of an operation. This convenient display location avoids the need for the surgeon to interrupt the procedure or to rely upon an assistant to obtain real time power information. Power control devices may also be carried by the handpiece.

A particularly beneficial feature of the surgical instruments of this invention is the provision of a safety switching assembly incorporated in the grip or handle portion of the instrument rather than the conventional foot switch. While the instrument is basically worn by the surgeon atop his wrist and forearm, a depending fixture is grasped by the hand. With the hand so positioned, two fingers, usually the index and middle finger of the hand, straddle a depending structural element. A normally open power switch, typically a photoelectric switch, is positioned for activation by the natural placement of the fingers when the instrument is grasped by the hand. A photoelectric sensor may be used as a transmitter-receiver tuned to switch to a closed circuit condition only when its transmitter signal contacts a substance with the characteristics of flesh. The switch thereby discriminates between flesh and all other materials normally encountered in an operatory. Thus, the power supply is normally off, and is turned on only when the instrument is positioned in the hand of the surgeon for use. The laser beam is inherently deactivated when the power is off.

Even with the power supply on and the instrument positioned in the proximity of the operative site, the laser beam is normally physically blocked by internal structure. That blocking structure is moved out of interference with the laser beam only by deliberate and continuous mechanical pressure exerted by the surgeon. Typically, a secondary shutter actuator mechanism is associated with the structural component gripped by the surgeon's hand. The default mode of the shutter is closed. Opening of the shutter requires finger or thumb pressure. A laser beam is thus projected from the instrument of this invention only when a surgeon first deliberately grasps the invention in its normal position of use and thereafter deliberately applies actuation pressure to the shutter control mechanism. The instrument is ideally configured so that the shutter control is only operable when the surgeon's hand is correctly positioned.

The housing of the instrument is structured with a first portion adapted to contain a laser tube. The laser tube and associated components comprise means operable to produce a surgical laser beam. The first portion is configured externally to rest atop the forearm of the user. The longitudinal central axis of that portion of the housing is thereby disposed approximately parallel the forearm. A second portion of the housing is structured with a longitudinal axis transverse the longitudinal axis of the first portion. This second portion carries a window at its distal end and contains internal components arranged as guide means to direct the laser beam emitted by the laser tube contained within the first portion of the housing along a beam path within the housing to exit the housing through the window. The secondary actuating structure is operably associated with a structure depending from the second portion of the housing. It includes a first element which is adapted to extend between the adjacent fingers of the hand of the user and a second element carried by the distal end of the first element adapted to be grasped by the hand of the user. As so arranged, the surgeon maintains the unencumbered dexterity of his fingers. His fingers can thus be rested or used to manipulate ancillary objects while still supporting the laser instrument.

A shutter mechanism of the type previously described is mounted within the housing in the path of the laser beam so that it normally blocks the beam path. A shutter control mechanism which is operable from the second element of the depending handgrip structure is operable by an actuating mechanism selectively to manipulate the shutter mechanism, thereby to either pass or block the laser beam according to the position of the user's hand with respect to the actuating mechanism. The shutter means is thus selectively movable in this fashion to unblock the beam path.

An umbilical cord extends from the proximal end of the housing to a remote power supply. Because the proximal end of the housing is positioned well away from the surgeon's wrist and fingers, utilities may be supplied in this fashion without noticeable interference. The umbilical cord carries appropriate electrical conductors and also carries flexible conduits to pass a cooling medium to the interior of the handpiece. Selected internal components of the instrument can thereby be cooled by circulating fluids.

The entire instrument may be embodied as a portable device including a power supply, all packaged in a compact carrying case.

BRIEF DESCRIPTION OF THE DRAWINGS

In the drawings which illustrate that which is presently regarded as the best mode for carrying out the invention.

DESCRIPTION OF THE ILLUSTRATED EMBODIMENTS

Figure 1:
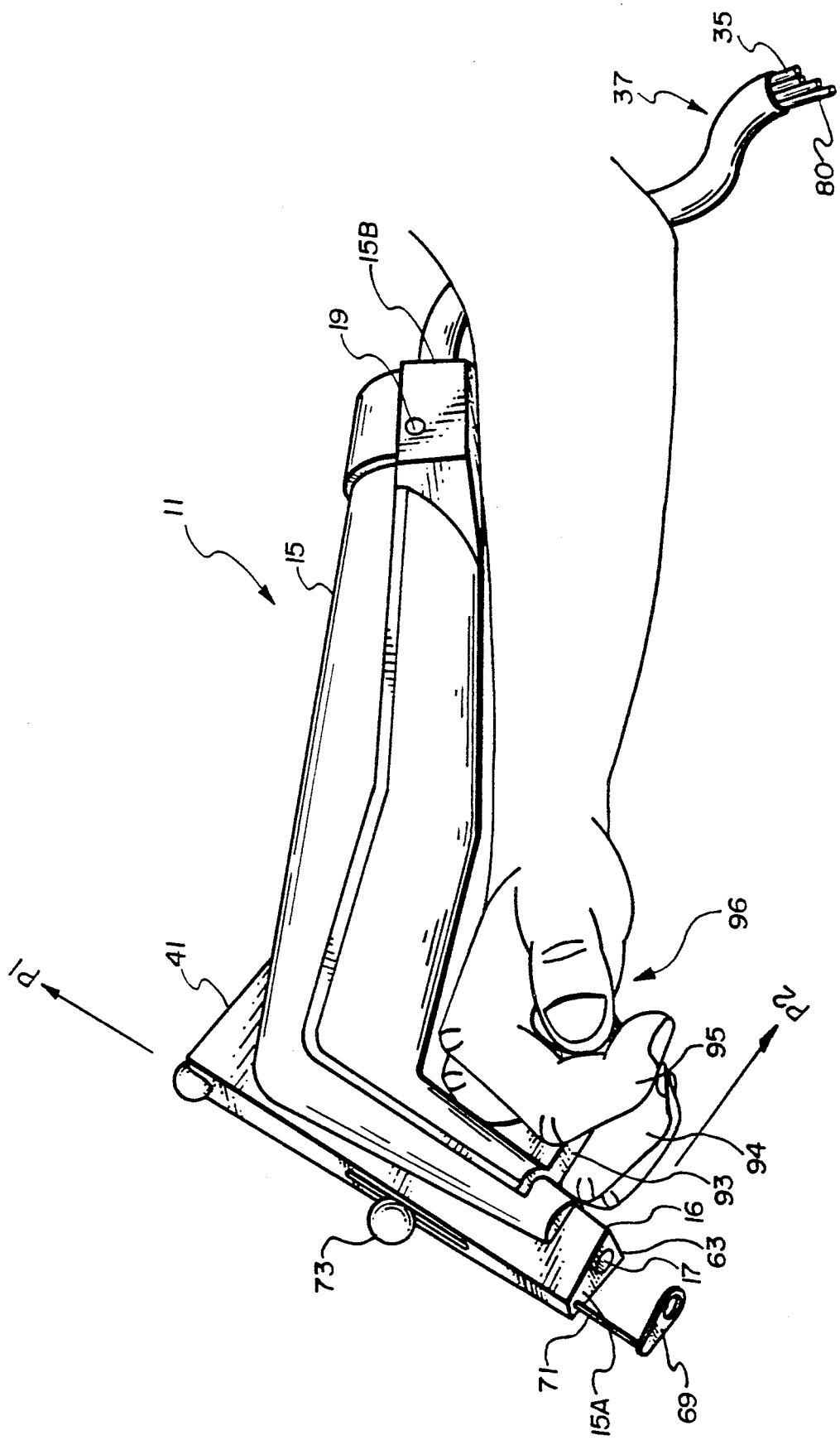
FIG. 1 is a perspective view of a typical laser surgical handpiece of this invention supported on the forearm of a user.

The drawings illustrate the invention embodied as a $CO_2$ laser instrument, designated generally 11. A laser tube 13 and other components are contained within a casing 15 constructed of a pair of mirror image plastic moldings 16, 17, which may be separated at the parting plane P, defined by the lines designated P1 and P2. Internal surfaces and bosses within the moldings 16, 17 hold all of the internal components in assembled condition when the moldings are held together by fastening screws, e.g. 19. The distal end 15A of the housing 15 is the working end of the instrument 11, while the proximal end 15B of the housing 15 is adapted to receive the utilities (gases, liquids, electronic signals, power) required for proper functioning of the instrument 11.

Figure 2:
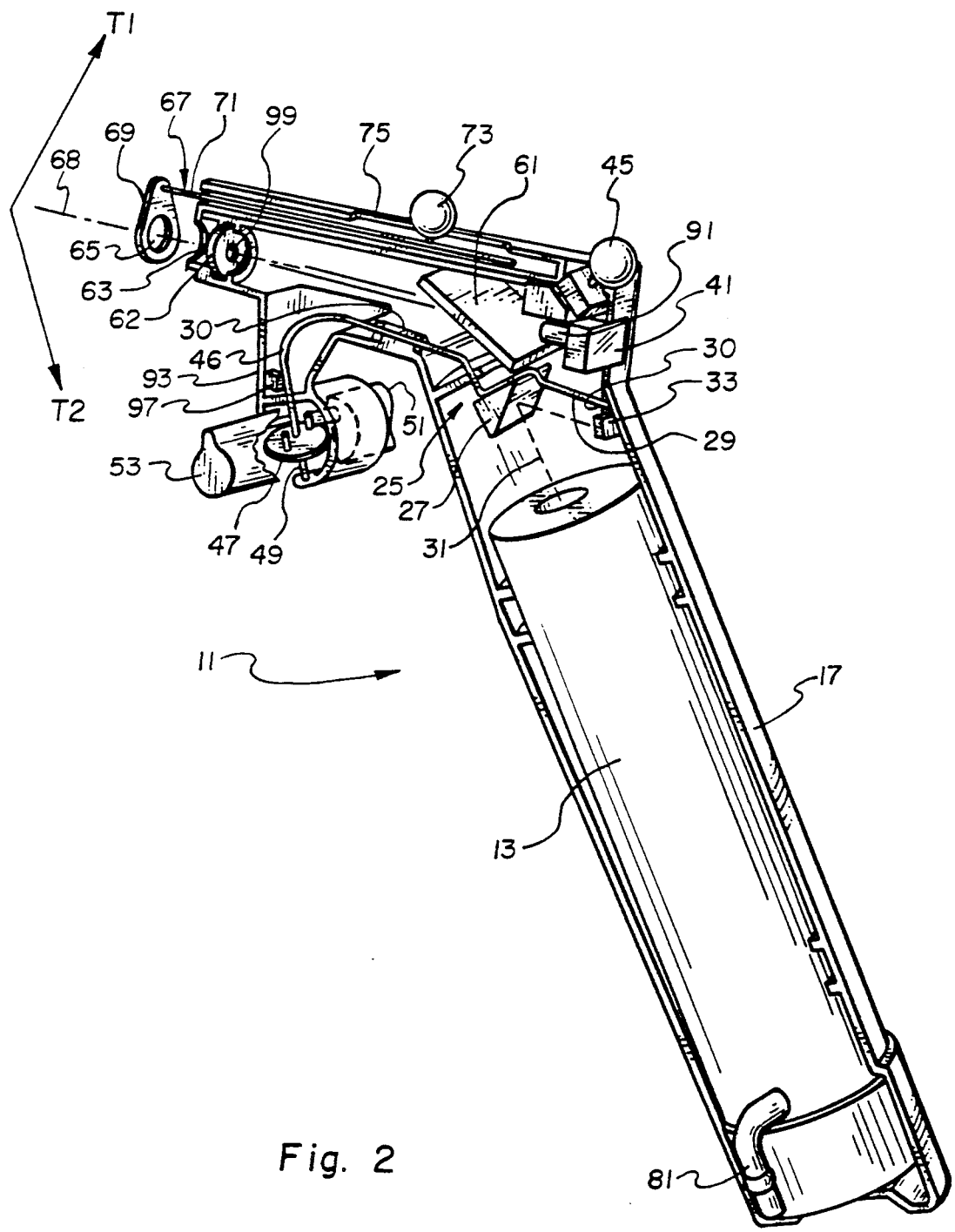
FIG. 2 is a view of the handpiece of FIG. 1 with half of its outer casing removed to expose internal components.
Figure 3:
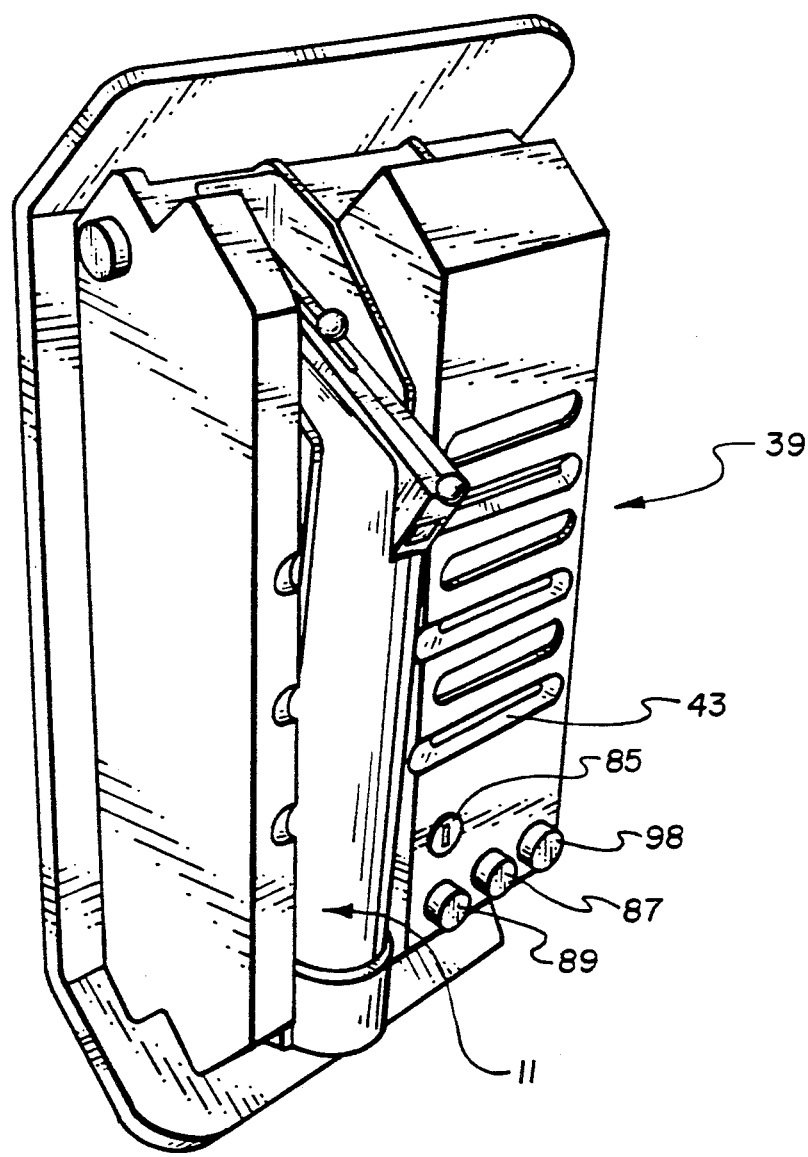
FIG. 3 is a perspective view showing a handpiece of this invention in association with a power supply and instrument panel in a portable instrument package.

FIG. 2 illustrates an internal shutter mechanism, designated generally 25, which includes a mirror element 27 mounted on a rigid shaft 29 which is pivotally mounted in bearings 30 at its opposite ends so that it may selectively be moved to intercept an emitted laser light beam 31 as shown. As so positioned, the light 31 is refracted to impinge upon a metering device, such as the Peltier cell 33 shown. Signals from the meter 33 may delivered through conductors 35 in the umbilical cord 37 to computing circuitry within the remote console, designated generally 39. Appropriate software associated with this circuitry converts the signals to direct power readings which may be displayed at either or both a display panel 41 of the instrument 11 or a display panel 43 of the console 39. A power control 45 may be provided a shown in the proximity of the display panel 41. The temperature of the Peltier cell 33 varies as it absorbs reflected light energy from the laser tube 13. In a specific embodiment, signals related to the temperature of the Peltier cell 33 are conveyed through the cord 37 to the console 39. A microprocessor or its equivalent is structured (programmed) to correlate those signals to power units (e.g. watts) and to transmit display signals back to the display panel 41.

The shutter mechanism 25 also includes a flexible shaft segment 46 driven by a turntable 47 which is mounted integral with a shaft 49 and functions as a cam element. The turntable 47 is rotated on the shaft 49 by finger pressure applied to either or both of the spring biased buttons 51, 53. As shown, inward longitudinal movement of either or both of the buttons 51, 53 causes rotation of the turntable 47 counterclockwise (viewed from above), thereby rotating the shaft 29 to swing the mirror 27 counter-clockwise (viewed from the meter 33). The mirror 27 is selectively coated to be opaque to the laser beam 31 but transparent to visible light. With the mirror 27 thus repositioned, the emitted light beam 31 strikes the mirror 61, from which it is refracted out through a lens 62, a window 63 and an aperture 65 of the distance gauge 67 as a focused laser beam 68. The beam 68 has a focal point on a target plane T, defined by the lines T1 and T2.

The distances of separation between the gauge plate 69 and the window 63 is adjusted through movement of the rod 71 by finger pressure on the knob 73. Travel of the knob 73 is limited by the slot 75, and the precise positioning of the plate 69 within this travel limit is maintained by frictional pressure exerted on the rod 71 by the moldings 16, 17 as best shown by FIG. I. Other embodiments within contemplation include racheting or other mechanisms for precise displacement of the gauge plate 69 with respect to the window 63. In any event, the gauge 67 is carried at the distal end 15A of the housing 15 and is operable to establish a minimum permissible separation between the distal end 15A and an operative site.

The umbilical cord 37 includes any necessary conductors 35 and tubing 80 required to transport electronic signals, power and coolant between the console 39 and the handpiece 11. Coolant is circulated in conventional fashion through the laser tube assembly 13 by introduction of coolant into an inlet 81, through the assembly 13 and out an outlet (not visible) opposite inlet 81. Suitable coolants include distilled water, ethylene glycol or other conventional cooling liquids or gases. Cooling may be provided to other components or regions within the handpiece 11, but the details of such cooling are not specifically significant to this invention. For example, if a Peltier cell is used as meter 33, it should be cooled to avoid permanent damage. A reservoir, pump and appropriate tubing for circulating coolant may be provided internal the console 39, together with a power supply and electronic control components. Again, the specific details of these elements and their arrangement are not critically important to this invention which resides in the compact arrangement of components in the handpiece 11 in association with a compact and portable remote console 39.

In a typical operation, a key switch 85 is turned to the "on" position. An initialization sequence is commenced by pressing the appropriate control button 87. The power delivered to the handpiece may be adjusted by means of a control knob 89. A high intensity aiming beam light source 91 is actuated through initialization, and projects an annular aiming beam through the mirror 61 coaxial with the aperture 65 and lens 62. The annular beam is focused by the lens 62 to the target plane T. The handpiece 11 is lifted from the console 39 thereby repositioning the target plane T and positioned as shown by FIG. 1 with a depending fixture 93 held between adjacent fingers 94, 95, when grasped by the hand 96 of a user. A light sensitive transmitter/receiver device (such as a normally open photocell) 97 is thereby blocked from light, resulting in a closed circuit which enables the laser assembly 13. The resulting laser beam 31 is deflected to the meter 33 so that the power delivered to the handpiece is displayed, e.g. through a seven segment display at the panel 41. The desired power level can be adjusted by either of the controls 89 or 45, as may be convenient. Selection of the actual control site, either base (console) or remote (handpiece), is accomplished by pressing a button 98. The gauge plate 69 may be set as desired with respect to the target plane T and/or the operative tissue site. In any event, when the surgeon is ready to apply the laser beam 68 to the operative site, he presses one or both of the buttons 51, 53 (usually 53 in the case of a right-handed individual, FIG. 1). The beam 68 is focused by the mirror 61 to pass through an aperture 99 of the lens 62. Its focal point is usually precisely at the target plane T, coplanar with the focal region of the aiming beam. The surgeon may orient the target plane T with respect to the operative site as appropriate during the procedure, relying upon the gauge plate 69 to limit the approach of the window 63 to the site.

As an additional safety precaution, the preferred embodiments are arranged to visually and audibly indicate when the laser beam is both enabled and unshuttered; that is, projected through the window 63. For example, the display at panel 41 may be caused to flash at intervals. Alternatively or concurrently, an alarm in the housing 15 or at the console 39 may emit steady or intermittent sounds during this period of actual laser projection.

Reference herein to details of the illustrated or other preferred embodiments is not intended to limit the scope of the appended claims which themselves recite the features regarded as important to the invention.

What is claimed is:

1. A laser surgical handpiece comprising: a housing including:
    a first portion adapted to contain a laser tube and configured externally to rest atop the forearm of a user such that the longitudinal central axis of said first portion may be disposed approximately parallel said forearm,
    a second portion with a longitudinal central axis transverse the longitudinal axis of said first portion, adapted to contain internal components arranged to direct a laser beam emitted by a laser tube contained within said first portion through a window disposed at a distal end of said second portion, and structure depending from said second portion including
    a first element adapted to extend between adjacent fingers of the hand of said user, and
    a second element carried by the distal end of said first element, said second element being adapted to be grasped by the hand of said user.

2. A handpiece according to claim 1 including a shutter mechanism mounted within said housing in the path of said laser beam wherein said second element of said structure contains a shutter control mechanism operable selectively to manipulate said shutter mechanism thereby to block or pass said laser beam according to the position of the user's hand with respect to said second element.

3. A handpiece according to claim 2, wherein said second element is configured as an approximately cylindrical hollow structure with a central axis spaced from and transverse the central axes of both said first and second portions.

4. A handpiece according to claim 3, wherein said cylindrical hollow structure contains:
    first mechanical switch means and second light-responsive switch means with an on mode and an off mode;
    said first switch means being actuated by thumb pressure applied by the user axially with respect to said cylindrical hollow structure; and
    the mode of said second switch means being reversed by placement of the user's hand in normal gripping relationship with respect to said cylindrical hollow structure, thereby to block light from said second switch means.

5. A handpiece according to claim 1, including power readout means carried by said housing.

6. A handpiece according to claim 5 including a shutter mechanism mounted within said housing in the path of said laser beam wherein said second element of said structure contains a shutter control mechanism operable selectively to manipulate said shutter mechanism thereby to block or pass said laser beam according to the position of the user's hand with respect to said second element, said power readout means being operably associated with power metering means disposed to intercept said laser beam when it is blocked by said shutter mechanism whereby said readout means is caused to display the power of said laser beam detected by said metering means.

7. A handpiece according to claim 5, further comprising:
    a Peltier cell operably associated with said power readout means and positioned for contact by a laser beam directed by internal components with said second portion of said housing;
    said Peltier cell and said power readout means being operably associated through detection circuitry and computing circuitry structured to detect heating of said Peltier cell by said laser beam to correlate said detected heating to power units and to display a power reading at said readout means.

8. A handpiece according to claim 7 in combination with a remote console, said console including said computing circuitry and being connected to said handpiece through an umbilical cord which constitutes means for conducting electronic signals between said handpiece and said console.

9. A handpiece according to claim 7 wherein said readout means is carried atop said housing.

10. A laser surgical handpiece comprising:
    a housing configured to rest atop the wrist and forearm of a user, said housing including a proximal end adapted to receive utilities from a remote location through an umbilical cord and a distal end adapted to deliver a surgical laser beam;
    a fixture integral with said housing adapted to be grasped by the hand of a said user when said housing is resting atop the wrist and forearm of said user;

laser generating means internal said housing operable to produce a surgical laser beam;

guide means within said housing arranged to direct a said surgical laser beam along a beam path within said housing to exit said housing at said distal end;

shutter means within said housing arranged normally to block said beam path and movable selectively to unblock said path; and actuator means associated with said fixture operable to move said shutter means to unblock said beam path.

11. A laser surgical handpiece according to claim 10 including a distance gauge carried at the distal end of said housing operable to establish a minimum permissible separation between said distal end and an operative site.

12. A laser surgical handpiece according to claim 11 wherein said distance gauge comprises a gauge plate with an aperture transverse said beam path external said housing.

13. A laser surgical handpiece according to claim 10 including means for projecting an annular aiming beam concentric to said surgical laser beam.

14. A laser surgical handpiece according to claim 13 wherein said annular light is of high intensity and is focused to the same plane as the focal point of said laser beam.

15. A laser surgical handpiece according to claim 14 including a distance gauge carried at the distal end of said housing operable to establish a minimum permissible separation between said distal end and an operative site.

16. A laser surgical handpiece according to claim 15 wherein said distance gauge comprises a gauge plate with an aperture transverse said beam path external said housing.

17. A laser surgical handpiece according to claim 16 wherein said annular aiming beam is projected through said aperture.

18. A handpiece according to claim 10 including a power readout means associated with said housing.

19. A handpiece according to claim 18 further comprising:

a Peltier cell operably associated with said power readout means and positioned for contact by a laser beam directed by internal components with said second portion of said housing;

said Peltier cell and said power readout means being operably associated through detection circuitry and computing circuitry structured to detect heating of said Peltier cell by said laser beam to correlate said detected heating to power units and to display a power reading at said readout means.

20. A handpiece according to claim 19 in combination with a remote console, said console including said computing circuitry and being connected to said handpiece through an umbilical cord which constitutes means for conducting electronic signals between said handpiece and said console.

21. A handpiece according to claim 20 wherein said readout means is carried atop said housing.

22. A laser surgical handpiece according to claim 21 including a distance gauge carried at the distal end of said housing operable to establish a minimum permissible separation between said distal end and an operative site.

23. A laser surgical handpiece according to claim 22 wherein said distance gauge comprises a gauge plate with an aperture transverse said beam path external said housing.

24. A laser surgical handpiece according to claim 21 including means for projecting an annular aiming beam concentric to said surgical laser beam.

25. A laser surgical handpiece according to claim 24 wherein said annular light is of high intensity and is focused to the same plane as the focal point of said laser beam.

26. A laser surgical handpiece according to claim 25 including a distance gauge carried at the distal end of said housing operable to establish a minimum permissible separation between said distal end and an operative site.

27. A laser surgical handpiece according to claim 26 wherein said distance gauge comprises a gauge plate with an aperture transverse said beam path external said housing.

28. A laser surgical handpiece according to claim 27 wherein said annular aiming beam is projected through said aperture.

* * * * *